(12) United States Patent
Olive et al.

(10) Patent No.: US 11,234,789 B2
(45) Date of Patent: *Feb. 1, 2022

(54) DEVICE AND METHOD FOR AUTOMATIC RECALIBRATION FOR 3D INTRAOPERATIVE IMAGES

(71) Applicants: MedTech S.A., Montpellier (FR); Lucien Blondel, Montpellier (FR)

(72) Inventors: Sebastien Olive, Montpelier (FR); Bertin Nahum, Baillargues (FR); Lucien Blondel, Montpellier (FR)

(73) Assignee: MedTech S.A., Montpellier (FR)

(*) Notice: Subject to any disclaimer, the term of this patent is extended or adjusted under 35 U.S.C. 154(b) by 84 days.

This patent is subject to a terminal disclaimer.

(21) Appl. No.: 16/868,139

(22) Filed: May 6, 2020

(65) Prior Publication Data

US 2020/0330180 A1    Oct. 22, 2020

Related U.S. Application Data

(63) Continuation of application No. 16/343,743, filed as application No. PCT/EP2017/077003 on Oct. 23, 2017, now Pat. No. 10,675,116.

(30) Foreign Application Priority Data

Oct. 21, 2016   (FR) ..................................... 1660264

(51) Int. Cl.
*G06K 9/00*     (2006.01)
*A61B 18/18*    (2006.01)
(Continued)

(52) U.S. Cl.
CPC ............ *A61B 90/361* (2016.02); *A61B 34/32* (2016.02); *A61B 90/39* (2016.02); *A61B 34/30* (2016.02);
(Continued)

(58) Field of Classification Search
USPC ........ 382/100, 103, 106, 128–133, 153–154, 382/162, 168, 173, 180–181, 189, 199,
(Continued)

(56) References Cited

U.S. PATENT DOCUMENTS 8,737,708 B2 *  5/2014  Hartmann ................. G06T 7/73
                                                    382/128
10,675,116 B2   6/2020  Olive et al.
(Continued)

FOREIGN PATENT DOCUMENTS

CA        2960528 A1    5/2017
CN        110352042 A   10/2019
(Continued)

OTHER PUBLICATIONS

"U.S. Appl. No. 16/343,743, Non Final Office Action dated Sep. 30, 2019", 23 pgs.
(Continued)

*Primary Examiner* — Seyed H Azarian
(74) *Attorney, Agent, or Firm* — Schwegman Lundberg & Woessner, P.A.

(57) ABSTRACT

The invention relates to a recalibration device (1) used during the acquisition of images of an anatomical area of a patient during robot-assisted surgery, including a body (3) made of radxoliacent material, which comprises fiducial markers (9) made of radiopaque material, said body (3) having a bearing surface (7) intended to be manually placed on a surface of said anatomical area of the patient. According to the invention, said fiducial markers (9) are arranged in a specific geometrical pattern enabling a certain detection of the positioning and orientation of the recalibration device (1) in a three-dimensional digital model built from the images derived from the acquisition of the anatomical area.

20 Claims, 6 Drawing Sheets

(51) Int. Cl.
*A61B 90/00* (2016.01)
*A61B 34/32* (2016.01)
*A61B 34/20* (2016.01)
*A61B 17/00* (2006.01)
*A61B 34/10* (2016.01)
*A61B 34/30* (2016.01)

(52) U.S. Cl.
CPC .................. *A61B 2017/0092* (2013.01); *A61B 2017/00725* (2013.01); *A61B 2017/00946* (2013.01); *A61B 2017/00991* (2013.01); *A61B 2034/105* (2016.02); *A61B 2034/2051* (2016.02); *A61B 2034/2055* (2016.02); *A61B 2034/2072* (2016.02); *A61B 2090/363* (2016.02); *A61B 2090/376* (2016.02); *A61B 2090/3945* (2016.02); *A61B 2090/3958* (2016.02); *A61B 2090/3966* (2016.02); *A61B 2090/3983* (2016.02); *A61B 2090/3991* (2016.02)

(58) Field of Classification Search
USPC ....... 382/219, 254, 276, 286–291, 305, 321; 257/415; 606/14, 130
See application file for complete search history.

(56) References Cited

U.S. PATENT DOCUMENTS

| | | | |
|---|---|---|---|
| 2007/0060799 A1 | 3/2007 | Lyon et al. | |
| 2010/0044808 A1* | 2/2010 | Dekker | B81C 1/00047 257/415 |
| 2010/0137880 A1* | 6/2010 | Nahum | A61B 34/30 606/130 |
| 2012/0201421 A1* | 8/2012 | Hartmann | A61B 6/5235 382/103 |
| 2013/0345718 A1* | 12/2013 | Crawford | A61M 5/172 606/130 |
| 2014/0350571 A1* | 11/2014 | Maillet | A61B 34/20 606/130 |
| 2016/0267659 A1 | 9/2016 | Vasey et al. | |
| 2017/0239002 A1* | 8/2017 | Crawford | A61B 17/1757 |
| 2019/0274775 A1 | 9/2019 | Olive et al. | |

FOREIGN PATENT DOCUMENTS

| | | |
|---|---|---|
| DE | 102010011589 A1 | 9/2011 |
| FR | 3057757 A1 | 4/2018 |
| WO | WO-2013192598 A1 | 12/2013 |
| WO | WO-2016058088 A1 | 4/2016 |
| WO | WO-2016148968 A1 | 9/2016 |
| WO | WO-2017064290 A1 | 4/2017 |
| WO | WO-2018073452 A1 | 4/2018 |

OTHER PUBLICATIONS

"U.S. Appl. No. 16/343,743, Notice of Allowance dated Jan. 29, 2020", 11 pgs.

"U.S. Appl. No. 16/343,743, Response filed Dec. 18, 2019 to Non Final Office Action dated Sep. 30, 2019", 9 pgs.

"European Application Serial No. 17798110.7, Response to Communication pursuant to Rules 161(1) and 162 EPC filed Dec. 9, 2019", 10 pgs.

"France Application Serial No. 1660264, Office Action dated Jun. 20, 2017", (W/ English Translation), 14 pgs.

"International Application Serial No. PCT/EP2017/077003, International Search Report dated Jan. 19, 2018", 5 pgs.

"International Application Serial No. PCT/EP2017/077003, Written Opinion dated Jan. 19, 2018", 5 pgs.

U.S. Appl. No. 16/343,743, filed Apr. 19, 2019, Device and Method for Automatic Recalibration for 3D Intraoperative Images.

"Canadian Application Serial No. 3,050,516, Office Action dated May 11, 2020", 4 pages.

"Canadian Application Serial No. 3,050,516, Response filed Sep. 11, 2020 to Office Action dated May 11, 2020", 13 pgs.

\* cited by examiner

DEVICE AND METHOD FOR AUTOMATIC RECALIBRATION FOR 3D INTRAOPERATIVE IMAGES

This application is a continuation of U.S. patent application Ser. No. 16/343,743, filed on Apr. 19, 2019, which is a U.S. National Stage Application under 35 U.S.C. 371 from International Application Serial No. PCT/EP2017/077003, filed on Oct. 23, 2017, and published as WO 2018/073452 A1 on Apr. 26, 2018, which claims priority to French Application No. 1660264, filed on Oct. 21, 2016, the benefit of priority of each of which is claimed hereby, and each of which are incorporated by reference herein in its entirety.

The present invention falls within the field of robot-assisted surgery, and relates more specifically to robot-assisted surgery implemented in complex anatomical areas, such as cerebrospinal surgery, in other words neurosurgery, and/or spine surgery.

In this context, the invention relates to a device and a method for recalibration between a reference system of a three-dimensional digital model derived from medical pictures and a reference system of an anatomical area of a patient during a robot-assisted surgery procedure. In the continuation of this document, a datum corresponds to a specific coordinate system of an element taking part in a recalibration and/or surgery procedure.

In this context, the recalibration device and the recalibration method of the invention permit to match a real position of the anatomical area of the patient with a three-dimensional digital model derived from medical pictures of the anatomical area of the patient.

Cerebrospinal surgeries focus on the major anatomical structures of the central nervous system, namely the brain and the spine. During operations in these particularly sensitive parts of the human body, the slightest operating error can have extremely serious consequences on the future physical and neurological autonomy of the patient. When performing cerebrospinal acts, it is essential that the surgeon's gestures be extremely accurate. Robot-assisted surgery is precisely responsible for assisting the surgeon with remarkable precision tools such as a surgical assistive robot-arm combining the positional rigor of the machines with the know-how of the operator.

The implementation of robot-assisted surgery generally requires the simultaneous operation of several separate tools or apparatuses, each comprising a specific reference coordinate system. The surgical operation itself is usually preceded by a preoperative or intraoperative sequence of imaging of the area of the operation, which is used by the surgeon to plan the actions related to the surgery. For both spatial and sequential reasons, it is important to cause the tools necessary for the operation to work in a common coordinate system, thus including a step of recalibration of the various reference systems of each element involved during the surgery, among which the anatomical area of the patient, a medical imaging system, and/or an operative monitoring system (including a navigation device and navigation targets) and/or a surgical assistive robot.

These recalibratien steps are essential for performing a robot-assisted surgical operation. Thus, the accuracy of the surgical procedure and, more generally, the success of the surgical operation highly depend on the precision of the recalibration steps between the anatomical working area and the various elements involved in the surgery. The recalibration steps must be as fast and smooth as possible so as to be perfectly integrated into the operating protocol to be implemented for the required operation. In addition, precise and automated recalibration steps permit the surgeon to concentrate on the operational tasks that are in the center of his know-how.

In addition, from the point of view of the patient and with regard to eventual post-operational effects, it is important that the operation is as less traumatic as possible, so that the patient recovers as soon as possible from the operation. Micro-invasive surgery develops in this context, with the primary objective of preserving as much as possible the anatomical tissues and structures located near the operated area. In order to achieve this goal, it is crucial that every step of the operational process, including the recalibration steps, be as less invasive as possible.

Presently, there exist a large number of techniques for recalibration between the reference system of an anatomical area of interest of the patient and that of the medical images of this anatomical area of interest. Each of these recalibration techniques uses a specific recalibration device as a patient reference system when acquiring images of an anatomical area of interest of said patient.

In general, such a recalibration device includes a radiolucent body provided with radiopaque fiducial markers and an optical target. The radiopaque fiducial markers permit to detect a position and an orientation of the recalibration device in the reference system of the medical images of the anatomical area of interest.

Among the known systems, a first type of recalibration device is described in U.S. Pat. No. 5,799,055. This first type of recalibration device includes a radiolucent body adapted to be carried by a surgical assistive arm. In order to perform a recalibration between the patient reference system and the reference system of the medical image, the radiolucent body is provided with eight radiopaque fiducial markers. The use of this type of recalibration device generates artefacts in the medical images when acquiring the anatomical area of interest of the patient. These artefacts are due to the assistive robot-arm and have the negative effect of making the identification of fiducial markers in medical images more complex, thus reducing the accuracy of the subsequent recalibration. Moreover, this device does not permit to carry out acquisitions of three-dimensional medical images.

A second type of recalibration device is described in U.S. Pat. No. 7,139,418. It comprises a radiolucent body provided namely with radiopaque fiducial markers arranged at determined locations. This radiolucent body is positioned at the level of the anatomical area of interest and in the field of view of the medical imaging acquisition system. The radiolucent body can be carried by a support rigidly connected to the operating table or carried by the end of a surgical assistive robot-arm. Thus, during the acquisition of the imaging data regarding the anatomical area of interest, it is possible to maintain the radiolucent body in an appropriate position predefined by the surgeon. This second type of recalibration device is coupled to at least one optical target including navigation markers that can be detected by a suitable navigation device. It should be noted that the spatial relationship between the radiopaque fiducial markers and the navigation markers is known. When the radiolucent body is supported by a robotic arm, the medical images have artefacts due to the robotic arm, which is not made of a radiolucent material. When the radiolucent body is carried by a support rigidly connected to the operating table, the attachment of the radiolucent body to the support slows down the operating process. Finally, this recalibration device is not compatible with the acquisition of a three-dimensional medical image of the anatomical area of interest.

A third type of recalibration device is described in U.S. Pat. No. 8,992,580. It includes a radiolucent body provided with radiopaque fiducial markers arranged at predetermined locations according to two different and parallel distribution planes. During the acquisition of the imaging data regarding the anatomical area of interest, this recalibration device is mechanically fastened to an anchoring part that is, in turn, fixed in a bone structure of the patient located close to the anatomical, area of interest. After the acquisition, the recalibration device is released from the anchoring part, which then accommodates a miniature surgical assistive robot for the following surgical operation. Thus, this recalibration device has the drawback of being fastened to an invasive anchoring part and may also cause a reduction in accuracy when the anchoring part moves during disassembling of the recalibration device and the assembly of the surgical assistive robot.

A fourth type of recalibration device, described in U.S. Pat. No. 8,104,958, includes a radiolucent body provided with radiopaque fiducial markers arranged at predetermined pyramidally organized locations. This recalibration device is placed and maintained manually by an operator in the field of vision of the medical imaging acquisition system, above the anatomical area of interest. This type of recalibration device also includes an optical or electromagnetic target. This target is provided with optical or electromagnetic navigation markers that can be detected by a suitable navigation device. This fourth type of recalibration device has indeed the advantage of being usable with a three-dimensional medical imaging system because of the pyramidal configuration of the radiopaque fiducial markers, but it has furthermore unacceptable drawbacks: the nursing staff is exposed to the radiation of the medical imaging systems, which is increasingly less accepted. In addition, since the recalibration device is maintained manually during the acquisition of medical imaging of the anatomical area of interest, the slightest instability is likely to cause problems in the sharpness of the medical images being generated, and thus a loss of accuracy of the subsequent recalibration.

A fifth type of recalibration device, for example described in U.S. Pat. Nos. 8,238,631, 8,644,570, 8,503,745 and 8,737,708, includes a radiolucent body provided with radiopaque fiducial markers arranged at predetermined locations according to a three-dimensional spatial organization. The radiolucent body also includes an optical target formed by optical navigation markers that can be detected by a navigation device. However, this type of device also has the drawback of using an invasive fastening technique, by clamping on a bone structure close to the anatomical area of interest.

A sixth type of recalibration device, described in U.S. Pat. No. 8,457,719, includes a flexible radiolucent body. The radiolucent body includes an upper face and a lower face. The lower face acts as a bearing surface intended to be placed on the anatomical area of interest of the patient. Said lower face of the radiolucent body is provided with an adhesive surface permitting to fasten the radiolucent body by gluing on soft tissues at the level of the anatomical area of interest. The radiolucent body furthermore includes active navigation markers arranged at predetermined locations. Thus, this type of recalibration device permits to create a digital surface model by detecting the active navigation markers, the digital surface model then being recalibrated with a three-dimensional medical imaging of the anatomical area of interest. This recalibration device has the advantage of being able to be used as a target for monitoring the movement of the anatomical area of the patient during a surgical procedure that would follow the recalibration. However, because of its positioning by gluing on soft tissues, any mechanical deformation of these soft tissues generates recalibration inaccuracies during the operating procedure. In addition, the active navigation markers require an on-board energy source, which namely causes sterilization problems. Finally, this type of recalibration device is for single use, which represents a high cost during each use and, from an economic point of view, clearly constitutes an additional drawback.

The present invention copes with the above-mentioned deficiencies of the prior art, by providing a high-precision sterilizable recalibration device enabling a recalibration of the various reference systems of each element involved during the surgery, namely for example: the anatomical area of the patient, a medical imaging system, a surgical monitoring system, a surgical assistive robot, etc.

In support of these aims, a first aspect of the invention relates to a recalibration device used during the acquisition of images of an anatomical area of a patient during robot-assisted surgery, conventionally including a three dimensional body made of radiolucent material, said body having an upper surface and an opposite surface forming a bearing surface to be placed manually on a surface of said anatomical area of the patient, said body comprises fiducial markers made of an radiopaque material. According to the invention, it is such that said fiducial markers are arranged between the upper surface and the bearing surface according to at least one specific geometrical pattern permitting a certain detection of the position and orientation of the recalibration device in a three-dimensional digital model constructed from the images derived from the acquisition of the anatomical area.

In practice, the specific geometric pattern formed by the radiopaque fiducial markers is a geometric pattern in which said radiopaque fiducial markers are organized asymmetrically. This or these specific geometrical patterns permit, within said three-dimensional digital model, a certain identification of a minimum number of radiopaque fiducial markers irrespective of the angle of view of the three-dimensional digital model. This certain identification of a minimum number of radiopaque fiducial markers permits to ensure a certain identification of the actual position and the orientation of the recalibration device resulting in a highly accurate recalibration between the three-dimensional model and the reference coordinate system of the anatomical area of the patient in the actual operating space.

According to an additional possibility, fiducial markers of one and the same geometrical pattern may be arranged in a coplanar way. Furthermore, the fiducial markers within one and the same geometric pattern can be organized asymmetrically. When the radiolucent body includes a plurality of different specific geometric patterns, the latter can then be organized in a plurality of planes parallel to each other. The use of specific geometric patterns organized in parallel planes permits to provide a larger number of fiducial markers in a reduced space. This compaction phenomenon ensures that all the fiducial markers are within the field of view of a medical imaging system.

According to one possible configuration, the radiopaque fiducial markers may furthermore have a spherical shape, for example with a diameter at least equal to 4 mm.

According to another advantageous feature, the recalibration device may include at least one navigation target provided with at least three navigation markers, the geometric relationship of which with the fiducial markers is predetermined. The navigation target permits in practice to detect the actual position of the recalibration device in a reference coordinate system of a navigation device.

To this end, the navigation markers can be accurately located by a conventional detecting method such as triangulation. A specific recalibration between the reference coordinate system of the navigation device and a reference coordinate system of a surgical assistive robot ensures the detection of the actual position of the recalibration device in the reference coordinate system of the surgical assistive robot.

According to a first variant, the navigation markers may be of the passive type. In a second variant, said navigation markers may be of the active type. In both variants, they may be optical navigation markers, or electromagnetic navigation markers.

According to an additional feature, the navigation markers can be placed on a support including fastening means removable with respect to the body of the recalibration device. Preferably, the support is a telescopic arm, which can take several positions. In each position, the geometric relationship between navigation markers and the fiducial markers is preferably predetermined.

According to an additional feature of the recalibration device of the invention, the latter may be provided with a stabilization system with respect to the body of the patient, for example made of a malleable material adaptable to the surface of the anatomical area and capable of maintaining the recalibration device in position during the data acquisition.

According to one possibility of the invention, the stabilization system can be formed by two flexible wedges. Each wedge may then be fastened in the vicinity of a side edge of the recalibration device or incorporated in the device. With such a configuration, the stabilization of the recalibration device occurs by bearing on the anatomy of the patient.

This feature is part of the overall approach to simplifying the operating process. Eliminating the invasive nature of the positioning of the recalibration device is clearly a factor of smoothing and acceleration of the operating process.

It should furthermore be noted that the non-invasive and quick positioning of the recalibration device therefore permits to reduce the immobilization time of a surgical room, which represents a significant reduction of the operating costs.

This represents furthermore a certain advantage from the point of view of the patient, since the non-invasive character can only facilitate the surgical effects, since it represents in reality one or more less incisions in his body, saving him the corresponding traumas.

A second aspect of the invention relates to an image-guided robot-assisted surgery system implementing a recalibration device according to the invention, as defined and explained above.

According to this second aspect of the invention, the robot-assisted surgery system comprises a surgical assistive robot-arm and a navigation system.

A third aspect of the invention relates to a method for acquiring and detecting an anatomical area of a patient for the preparation of a surgical procedure using a recalibration device according to the first aspect of the invention in a robot-assisted surgery system defined by the second aspect of the invention.

This method of acquiring and detecting an anatomical area of a patient is characterized in that it includes:
A step of preparation the acquisition of images of the anatomical area of the patient including the installation of a patient, a three-dimensional navigation system, a medical imaging system and a surgery assistive robot-arm, A step of manually placing the recalibration device on a surface of an anatomical area of the patient and in a field of view of a medical imaging system, A step of acquiring a position of the recalibration device by the navigation system, A step of acquisition by the navigation system of a position of a target for operative monitoring of the anatomical area of the patient, A step of putting into safety the nursing staff, A step of acquiring images of the anatomical area of the patient and the recalibration device positioned on the surface of the anatomical area of the patient, A step of building a three-dimensional digital model from the medical images obtained during the step of acquiring the anatomical area of the patient, A step of identifying radiopaque fiducial markers integrated in the recalibration device, A step of calculating the recalibration, A step of displaying the recalibrated three-dimensional digital model, and A step of planning the operation using the recalibrated three-dimensional digital model.

The use of the recalibration device according to the first aspect of the invention is part of an approach aimed at smoothing and accelerating the method of acquiring and detecting an anatomical area of a patient.

Other peculiarities and advantages will become evident in the detailed and non-restrictive description of three exemplary embodiments of the invention, illustrated by FIGS. 1 to 9 attached hereto and in which.

Figure 1:
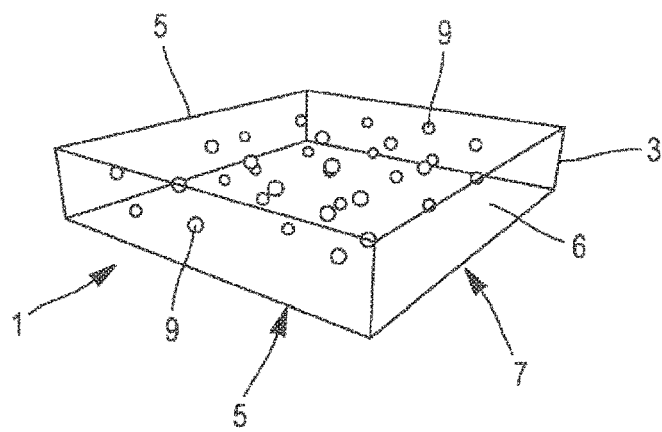
FIG. 1 is a perspective view of a recalibration device according to a first embodiment of the invention, this representation showing the radiopaque fiducial markers arranged inside the radiolucent body.

The representations object of the figures show different aspects of several possible models, knowing that they are only given by way of an example, and that other configurations are also covered by the invention. All these representations relate to a recalibration device 1 used during the acquisition of medical images of an anatomical area 2 of interest of a patient. The anatomical area 2 of interest corresponds in fact to the anatomical area 2 on which the surgeon carries out a surgical operation.

It should be noted that in the continuation of this document, the term reference system is used to designate the expression "reference coordinate system".

During the acquisition of medical images, the use of a recalibration device 1 positioned at the level of the anatomical area 2 of interest permits to recalibrate all the reference systems of the elements involved in the future surgery with the reference system of the three-dimensional digital model obtained from the medical images. In other words, said use permits to recalibrate the reference system of the three-dimensional digital model with the reference system of the patient and the reference system of a navigation system so as to locate the actual position of the anatomical area 2 of interest in the reference system of the navigation system. Then, a recalibration of the reference systems of the navigation system and of the robotic arm permits to determine the position of the anatomical area 2 of interest in the reference system of the robotic arm. The conditions are then in place for the surgical operation to begin.

With this in mind and as illustrated in FIGS. 1 to 12, the recalibration device 1 is comprised of a parallelepipedal body 3, in this case a rectangular body in the form of a plate. The plate includes an upper face 4 opposite a lower face 5, the lower 5 and the upper 4 faces forming the long sides of the plate and being connected by side edges 6. The lower face 5 of the plate constitutes a bearing surface 7 of the recalibration device 1 intended to be placed manually on the anatomical area 2 of interest of the patient.

The body 3 of the recalibration device is a radiolucent body 3 made of a sterilizable radiolucent material such as, for example, polyetheretherketone, generally referred to as "PEEK". As illustrated in FIGS. 1 to 11, the body 3 of the recalibration device 1 includes radiopaque fiducial markers 9, the radiopacity resulting from the properties of the material of which they are made (for example of metal). In the present case, the radiopaque fiducial markers 9 are simply formed of spheres of a common diameter, for example equal to 4 mm. In order to be identifiable, the fiducial markers 9 must have dimensions meeting several constraints. More specifically, the dimensions of the fiducial markers 9 must be sufficiently large to be identifiable in medical images without, however, influencing the dimensions of the recalibration device 1. The latter must in addition remain compact in order to maintain its practical use and its maneuverability. In this context, each fiducial marker 9 can then have a diameter between 3 mm and 5 mm, and preferably a diameter of 4 mm. In addition, as soon as they are detectable on medical images, each fiducial marker 9 may have shapes and dimensions that may be identical or different. In the present case, these radiopaque fiducial markers 9 are arranged inside the body 3 of the recalibration device 1.

In the exemplary embodiments illustrated in FIGS. 1 to 12, the fiducial markers 9 are arranged in one and the same plane at predetermined locations in a specific geometric pattern. Preferably, within a specific geometric pattern, the fiducial markers 9 are organized in an asymmetric geometric pattern. The asymmetric nature of the arrangement of the fiducial markers 9 in a specific geometric pattern has the advantage of ensuring, irrespective of the viewing angle, a certain identification of a minimum number of fiducial markers 9 within a three-dimensional digital model built from the images derived from the acquisition of the anatomical area. This certain identification of the fiducial markers 9 ensures a certain detection of the position and the orientation of the recalibration device in a three-dimensional digital model built from the images derived from the acquisition of the anatomical area.

In order to further increase the possibilities of detection of the fiducial markers 9 in operating pictures, the recalibration device 1 includes several specific geometrical patterns. Advantageously, these specific geometrical patterns are different from each other and organized in parallel planes, each geometric pattern corresponding to a given plane and containing a predetermined number of fiducial markers 9. This organization into different geometric patterns positioned according to parallel planes provides several advantages to the invention: on the one hand, it ensures a better identification of the fiducial markers 9 in operating pictures, and on the other hand it permits to preserve a compact nature of the recalibration device 1.

Figure 2:
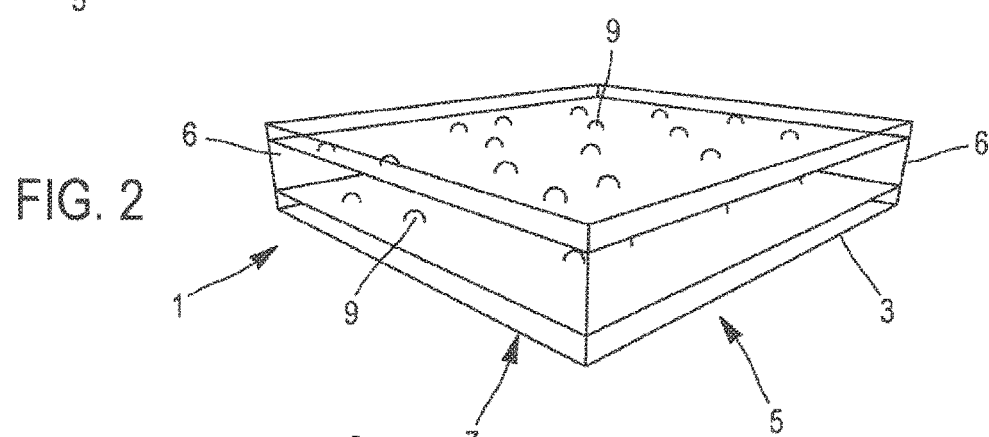
FIG. 2 is a perspective view of the recalibration device of FIG. 1, in which the planes for organizing the radiopaque fiducial markers are schematically illustrated.
Figure 3:
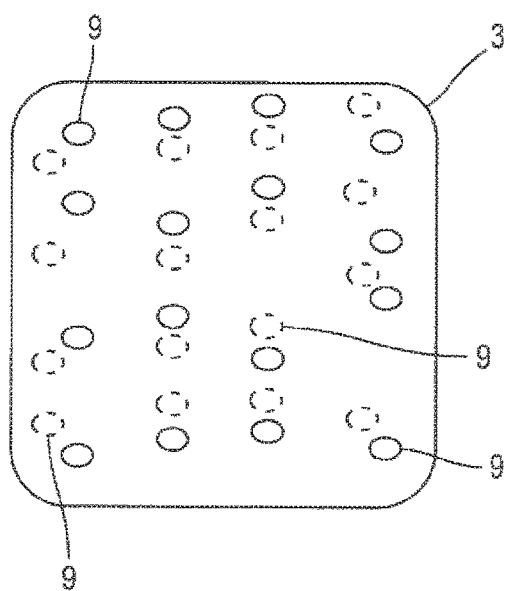
FIG. 3 is a schematic representation of a cross-section of the device of FIG. 1, in which the fiducial markers are organized according to two organizational planes.

More particularly, in the configuration shown in FIGS. 2 and 3, the fiducial markers 9 are arranged according to two specific geometrical patterns respectively arranged on two parallel planes. As illustrated in FIG. 3, each geometric pattern organizes the fiducial markers 9 in a different way: a first geometric pattern is represented by its fiducial markers 9 illustrated by continuous circles, whereas a second geometric pattern includes fiducial markers 9, which are represented by discontinuous circles. The fiducial markers 9 of the second geometric pattern do in no configuration overlap the fiducial markers 9 of the first geometric pattern, thus minimizing the identification errors of said fiducial markers 9 in the three-dimensional digital model generated from the medical images.

In general, a system for acquiring three-dimensional medical images carries out a multitude of two-dimensional pictures in order to build a three-dimensional volume of the anatomical area 2 of interest. The data contained in this three-dimensional volume are then processed so as to generate a three-dimensional digital model of the anatomical area 2 of interest. In this case, the three-dimensional reconstruction uses the same type of two-dimensional sections derived from the three-dimensional volume generated by the medical image acquisition system. These sections are then assembled according to a number of criteria such as the thickness and the distance between each section, which must be homogeneous in a series in order to build a three-dimensional model that is as faithful as possible.

According to an additional feature of the invention, each fiducial marker 9 may have predetermined specific dimensions. This property further reduces the likelihood of confusion during the detection of the fiducial markers 9 in the operating pictures by adding additional recognition data of said radiopaque fiducial markers 9, which data depend on the dimensions.

In the example illustrated in FIGS. 4 to 10, the recalibration device 1 includes navigation markers 10 located in the vicinity of the upper face 4 of the radiolucent body 3. In the present case, the navigation markers 10 are navigation markers 10 of the optical type, i.e. they can be detected by an optical navigation system. Preferably, these inactive optical navigation markers 10 are formed of reflective spheres. The reflective spheres are covered with a coating, which is advantageously sterilizable and reflects light and more particularly the infrared rays. In order to further improve their recognition, each reflective sphere may have its own dimensions.

According to a variant of the invention, an active-type optical navigation marker 10 may also be chosen. In this case, it can be formed of a light-emitting diode referred to as "LED". Unlike an inactive optical navigation marker 10, which is detectable by an optical navigation system due to the nature of its external coating, an active optical navigation marker 10 is visible by an appropriate optical system only when it is powered by an energy source.

According to another variant of the invention, a navigation marker 10 may be chosen of the electromagnetic type, capable of being detected by an electromagnetic navigation system. According to a possible example, it may be induction coils immersed in a magnetic field.

Finally, due to the known geometric relationship between the fiducial markers 9 and the navigation markers 10 of a recalibration device 1, it is possible to locate the position and the orientation of the recalibration device 1, and hence the anatomical area 2 of the patient by a navigation system.

For reasons relating to the quality of the location of the actual position and orientation of the recalibration device 1, the latter must include at least three navigation markers 10 arranged in a predetermined spatial configuration. Advantageously, as already mentioned, each navigation marker 10 can furthermore also have different dimensions, permitting to identify it more quickly and with certainty.

The navigation markers 10 are fixed in the vicinity of one of the edges 6 of the radiolucent body 3 of the recalibration device 1. They may depend on a support 11 different from the body 3 of the device 1 of the invention. Preferably, in this case, the support 11 of these navigation markers 10 is made of a radiolucent material.

Figure 4:
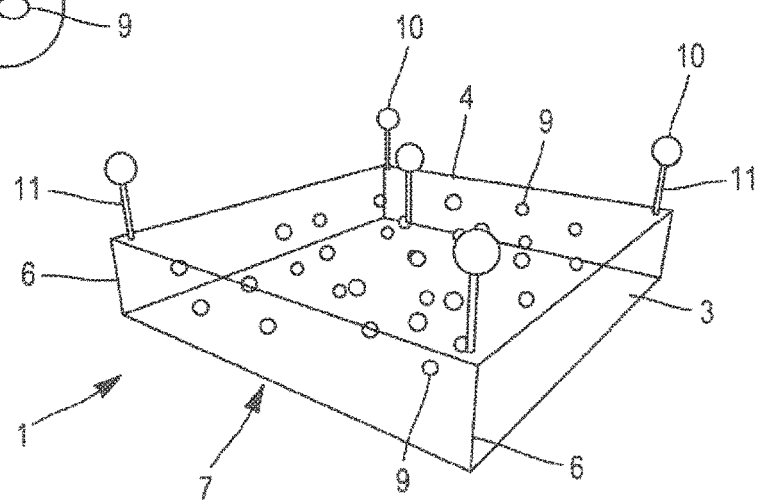
FIG. 4 is a perspective view of the recalibration device of FIG. 1 provided with a navigation target.
Figure 9:
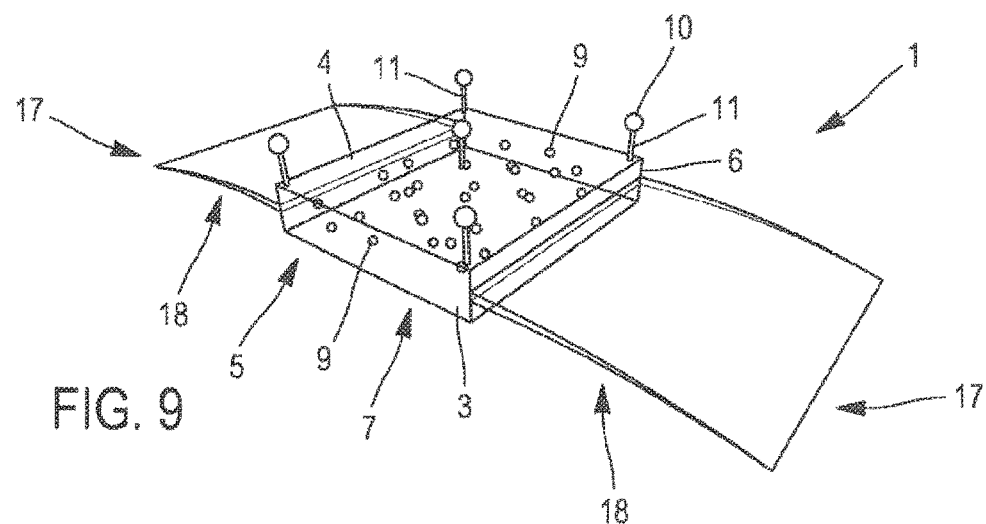
FIG. 9 is a perspective view of the recalibration device of FIG. 8, in which the radiolucent body is provided with another navigation target.

As illustrated in FIGS. 4 and 9, the recalibration device 1 includes five navigation markers 10 spatially arranged in a cross-shaped pattern with diagonal legs. A navigation marker 10 is arranged in the center and the other four are placed at each corner of the body 3. In the configuration shown in these figures, each optical navigation marker 10 is individually fixed to the radiolucent body 3 of the recalibration device 1 through a rod-shaped support 11.

In the variant illustrated in FIGS. 5 to 8 and 10, the navigation markers 10 include a support 11 with four legs. At each of the ends of each leg is arranged a navigation marker 10 forming a navigation target 12, which can be oriented in a predetermined direction. According to this exemplary configuration, the navigation target 12 may be in the form of a four-leg cross (as illustrated in FIGS. 5, 6, 8 and 10).

Figure 5:
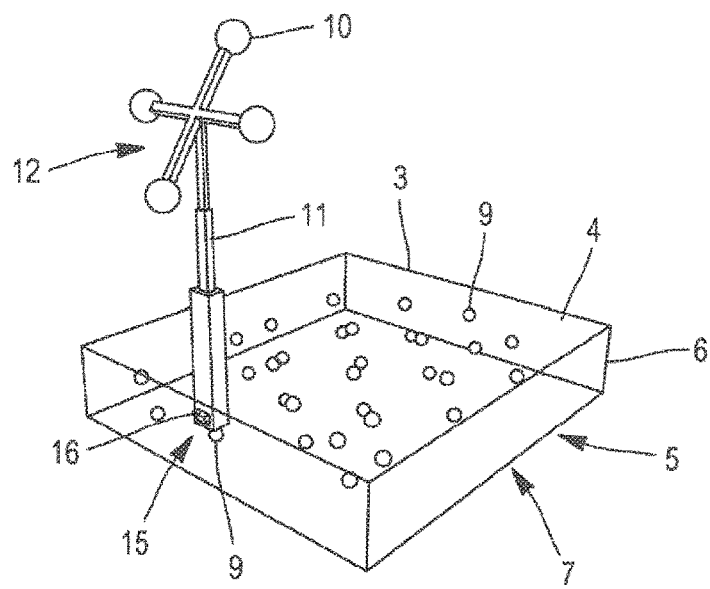
FIG. 5 is a perspective view of the recalibration device of FIG. 1 provided with another type of navigation target.
Figure 6:
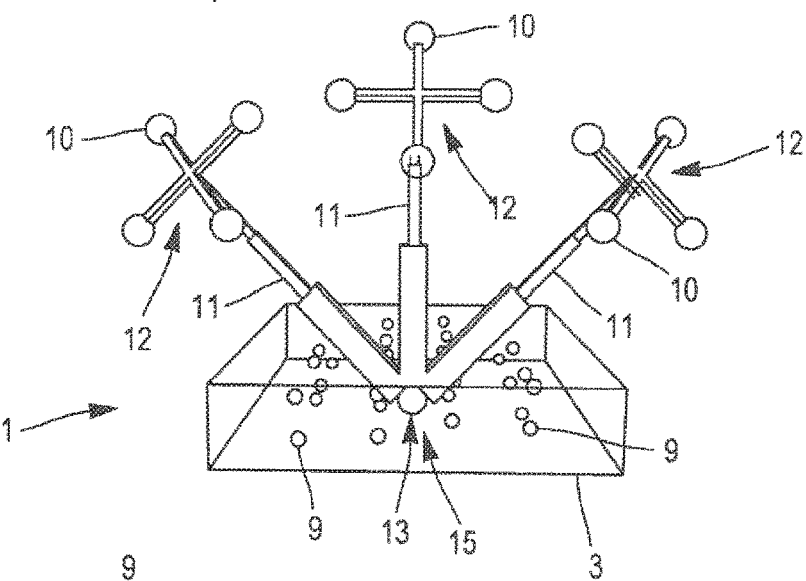
FIG. 6 is a perspective view of the recalibration device of FIG. 1 provided with yet another type of navigation target.
Figure 7:
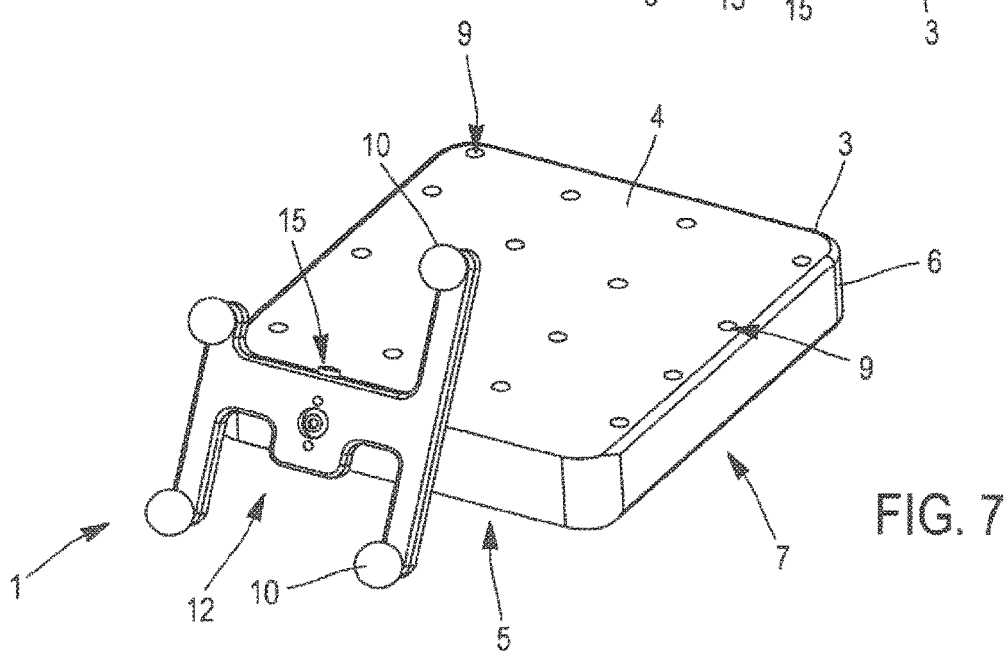
FIG. 7 is a perspective view of the recalibration device of FIG. 1, in which the recalibration device includes a support fastened in the vicinity of the radiolucent body.

According to a particular feature illustrated in FIGS. 5 and 6, the support 11 is formed by a telescopic arm, which can adopt several positions by axial longitudinal translation. In each position, the geometric relationship between the navigation markers and the fiducial markers 9 is known.

Figure 12:
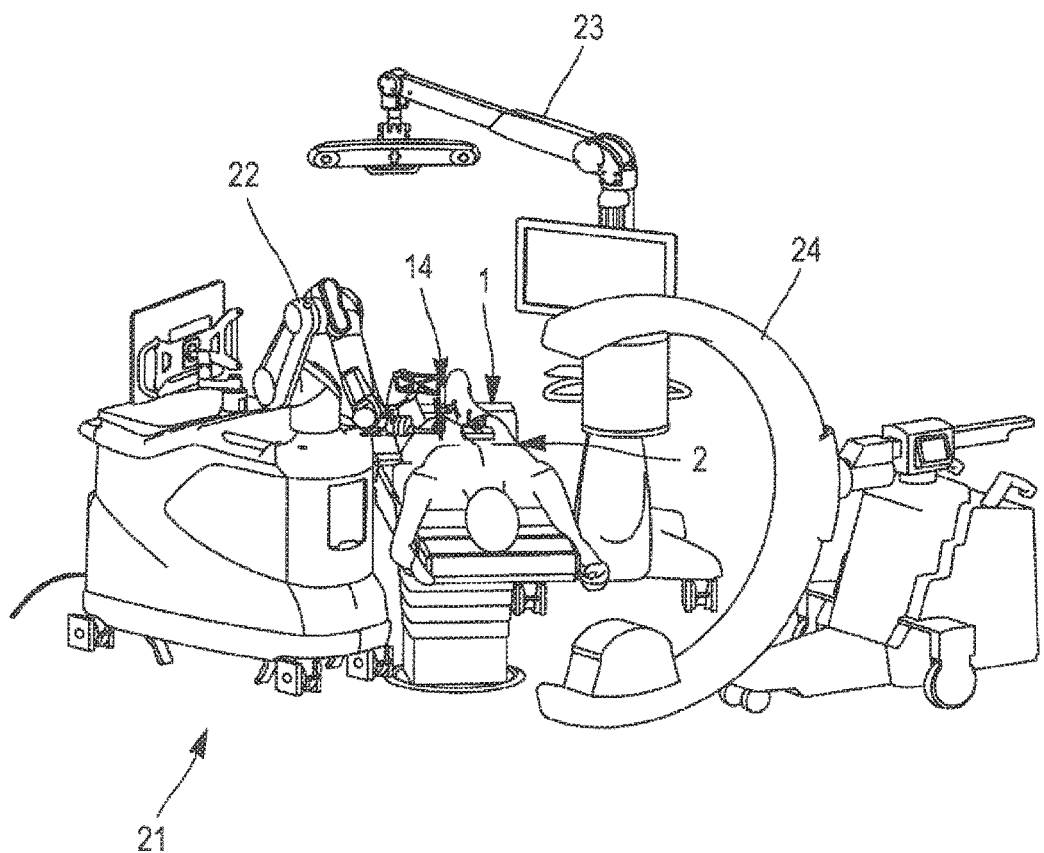
FIG. 12 is a representation of a robot-assisted surgery system in which a recalibration device according to the invention is used.

In the particular case of FIG. 6, the support 11 is connected at one of the edges 6 by means of a pivotal fastening 13 permitting the navigation target 12 to take several known positions, in this case three positions. This feature permits to vary the orientation of the target 12 and avoids any problem of masking and/or confusion with navigation markers of an operative monitoring target 14 anchored in a bone near the anatomical area of interest (as illustrated in FIGS. 10 and 12).

The support 11 furthermore includes removable fastening means 15, which can preferably be manipulated without tools, with respect to the body 3 of the recalibration device 1. In the present example, the removable fastening means 15 are formed by a clip 16 (illustrated in FIGS. 5 and 6). However, the removable fastening means 15 can also be formed by any means (for example a screw) permitting, on the one hand, to hold the support 11 with certainty in its position and, on the other hand, to remove it at will and manually.

Figure 8:
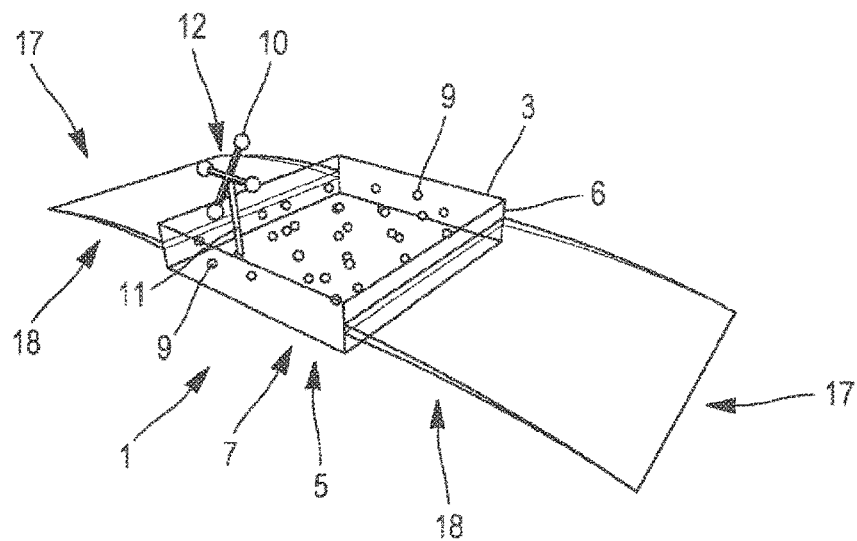
FIG. 8 is a perspective view of a recalibration device according to a second embodiment of the invention, in which the radiolucent body is provided with a stabilization system.
Figure 10:
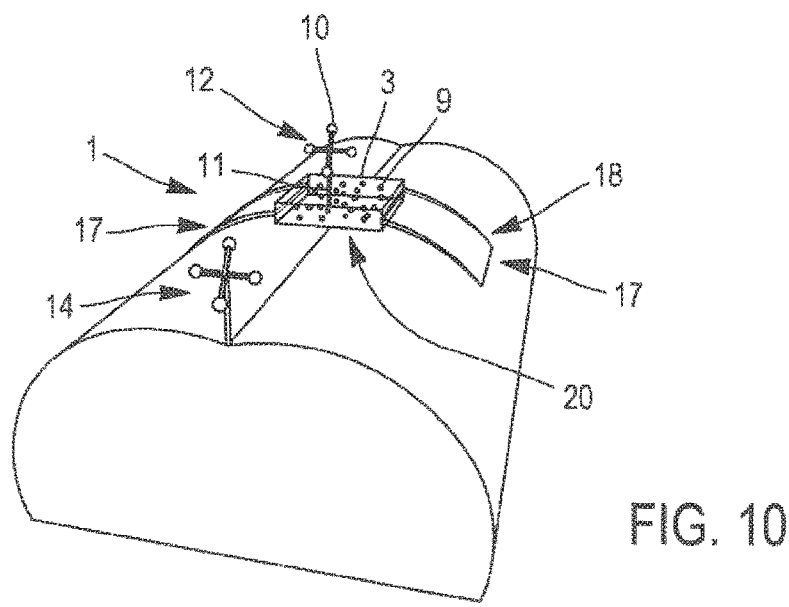
FIG. 10 is a perspective view of the recalibration device of FIG. 8 arranged at the level of an anatomical area of interest of a patient, in this case its spine.

In the examples illustrated in FIGS. 8 to 10, the recalibration device 1 is provided with a stabilization system 17 capable of being adapted to the morphology of the anatomical area 2 of the patient. The stabilization system 17 is in this case formed by two side wings with a curved shape forming wedges 18. Each wedge 18 is fixed in the vicinity of a side edge 6 of the recalibration device 1. Preferably, each wedge 18 is connected to the recalibration device through an articulated mechanical junction permitting the wedges 18 to pivot and to adapt themselves to the morphology of the patient.

The two wedges 18 placed on both sides of the body 3 cooperate in stabilizing the recalibration device 1 by resting on the anatomy of the patient. Their slightly curved configuration and the symmetry of their arrangement with respect to the body 3 of the recalibration device 1 of the invention permit to exert on the anatomical area 2 resulting forces comprising vertical, i.e. parallel components, oriented downwards, favoring the stabilization by gravity, and opposite horizontal components, which work together to maintain the recalibration device 1 relative to the body of the patient.

According to another possibility of the invention, the stabilization system 17 is made of a malleable, at least flexible, and sterilizable material capable of being adapted to the morphology of the patient. In order to maintain the recalibration device 1 in a stable position during the acquisition of the images, the malleable material used also has a certain mechanical rigidity. This stabilization system 17 permits an immediate manual positioning of the recalibration device 1 at the level of the anatomical area 2 of interest of the patient. By means of a simple manual application by the operator, the shape of the stabilizing system 17 can be "shaped" so as to fit the morphology of the patient.

During the acquisition of the medical images, said stabilization system 17 is sufficiently strong to keep the recalibration device 1 stable, in a suitable position, and in a non-invasive manner. This stabilization system 17 thus provides a great simplicity of installation, also contributing to increase the speed and the smoothness of the installation procedure, while maintaining a non-invasive nature that is eminently beneficial for the patient.

Figure 11:
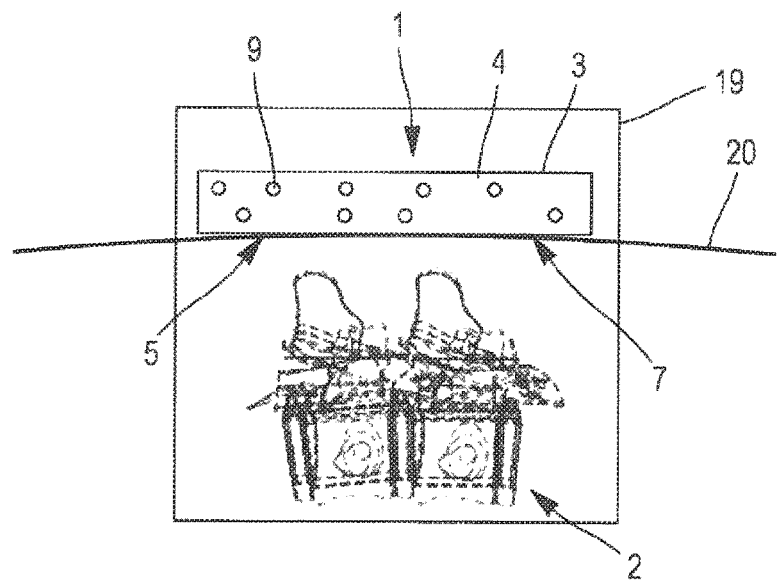
FIG. 11 is a representation of a lateral cross-section of the recalibration device arranged at the level of an anatomical area of interest.

As shown in FIG. 11, the recalibration device 1 has calibrated dimensions so that it is fully integrated into a field of view 19 of a medical imaging system. The aim of this calibration is to facilitate the identification of a maximum number of fiducial markers 9 by adapting the recalibration device 1 to the field of vision 19 of the imaging system, which it has in principle to operate with. In this specific case, the recalibration device 1 rests on a surface 20 of the anatomical area of interest 2, in this case on the skin of the patient. The field of view 19 of the medical imaging system includes the entire recalibration device 1 and also the anatomical area of interest 2, in this case the patient's spine.

In the example illustrated in FIG. 12, the use of the recalibration device 1 fits into the broader scope of an imaging-guided robot-assisted surgery system 21.

In this case, said system 21 includes a robotic arm 22 for surgical assistance, preferably a robotic arm having six degrees of movability, a navigation system 23, preferably an optical navigation system, and also a conventional three-dimensional medical imaging acquisition system 24 of the C-arm type in the illustrated example. This surgical system 21 permits to accompany the surgical procedure by displaying in real time an image of a three-dimensional digital model of the anatomical surfaces and the images of the related (axial, coronal and sagittal) cross-sections in which the position and/or the action of the surgical tools can be observed on screens coupled to the robotic arm 22 and to the navigation system 23.

In the context of a surgical operation carried out with this surgical system 21 illustrated in FIG. 12, in this case for spinal surgery, the patient is placed in the prone position, i.e. on his stomach, so that his spine is available for positioning the recalibration device 1.

The surgical procedure includes a real-time operative monitoring based on a navigation system 23 and an operative monitoring target. In the example illustrated in FIG. 10, the operative monitoring target is a target 14 that is implanted in a bone portion of the patient's spine during the preparation of the patient. This operative monitoring target 14 permits to monitor the movements of the patient during the entire operating protocol. The navigation device is adapted to locate optical navigation markers in a three-dimensional coordinate system, the navigation system 23 of which is the origin. As a result, the navigation device 23 permits namely to detect and monitor the movements of the tracking target 14 anchored in the spine, which permits to keep under control the trajectory of the robotic arm 22, which depends on the movements being detected. The movements being detected can be displacements of the spine resulting from the respiration of the patient or from the efforts exerted by the surgeon.

The operative monitoring target 14 also permits to detect the position of the patient relative to the position of the recalibration device 1 and thus to locate the actual position of the patient with respect to the recalibration device 1.

The navigation system 23 can also be used during the acquisition of the images in order to check that the recalibration device 1 does not move. If a movement is detected, a warning is issued to the user's address, asking him to restart a new procedure for acquiring the images of the anatomical area 2 of interest.

The surgical procedure using the robot-assisted surgery system 21 also includes a step of recalibrating the robot and the navigation system 23 by optical recalibration. To this end, an optical target is positioned at the end of the robotic arm 22. The robotic arm 22 provided with the optical target then adopts at least three predefined positions around the operating field. During this detection, the navigation system 23 locates the robotic arm 22 in its reference system. At the same time, the navigation system 23 checks that a navigation target fixed to the robot remains immobile, which means that the base of the robot does not move. In the opposite case, i.e. in the case of movements of the base of the robot, a new robot/navigation system recalibration is performed.

Another step of the operating procedure obviously consists in putting the patient under anesthesia, and also under respiratory apnea throughout the complete duration of acquisition of the medical images. This step permits to limit the respiratory movements of the patient, thus improving the sharpness of the images resulting from the acquisition of the patient's anatomical area of interest.

In order to locate the actual position of the patient on the operating table, the navigation system 23 carries out a recalibration in its reference system of the operative monitoring target 14. The coordinates of the operative monitoring target 14 can then be transposed into the reference system of the robotic arm 22 through the specific recalibration between the robotic arm 22 and the navigation system 23.

At this stage begins, the acquisition and detection of the anatomical area 2 of interest: during this phase, the recalibration device 1 of the invention finds its usefulness. This phase permits in practice to accurately locate the position of the anatomical area 1 of interest in the reference system of the navigation device 23 and indirectly of the robotic arm 22.

The acquisition phase includes a step of positioning the recalibration device 1 at the level of the anatomical area 2 of interest. To this end, the surgeon or an operator manually places and positions the recalibration device 1 of the invention on the back of the patient. More specifically, the recalibration device 1 is placed, in the field of vision 19 of the medical imaging system 24, at the level of the anatomical area 2 of interest, the one that will be subjected to a surgical operation, for example at the level of a vertebra.

The nursing staff is then put in safety in order to be protected from the ionizing rays, which are emitted during the acquisition of data on the anatomical area 2 of interest, while the recalibration device 1 is in position. This acquisition is carried out by a conventional three-dimensional medical imaging acquisition system, for example of the "O-arm" or "C-arm 24 type".

This acquisition phase is followed by a step of building an intraoperative three-dimensional digital model of the anatomical area 2 of interest from two-dimensional medical images according to a single type of cross-section, for example axial cross-section. This building step consists in assembling the two-dimensional medical images, for example in the framework of a "multi-planar reconstruction".

A step of detection of the radiopaque fiducial markers 9 within the intraoperative three-dimensional digital model is then implemented. It is carried out by an operator, for example the surgeon, on a control screen. The fiducial markers 9 can be identified in medical images because of their radiopaque nature and the specific geometric pattern according to which they are organized. Thus, during the acquisition of the anatomical area 2 of interest, a ghost image of each fiducial marker 9 is generated in the form of a white spot with a certain luminous intensity.

Figure 13:
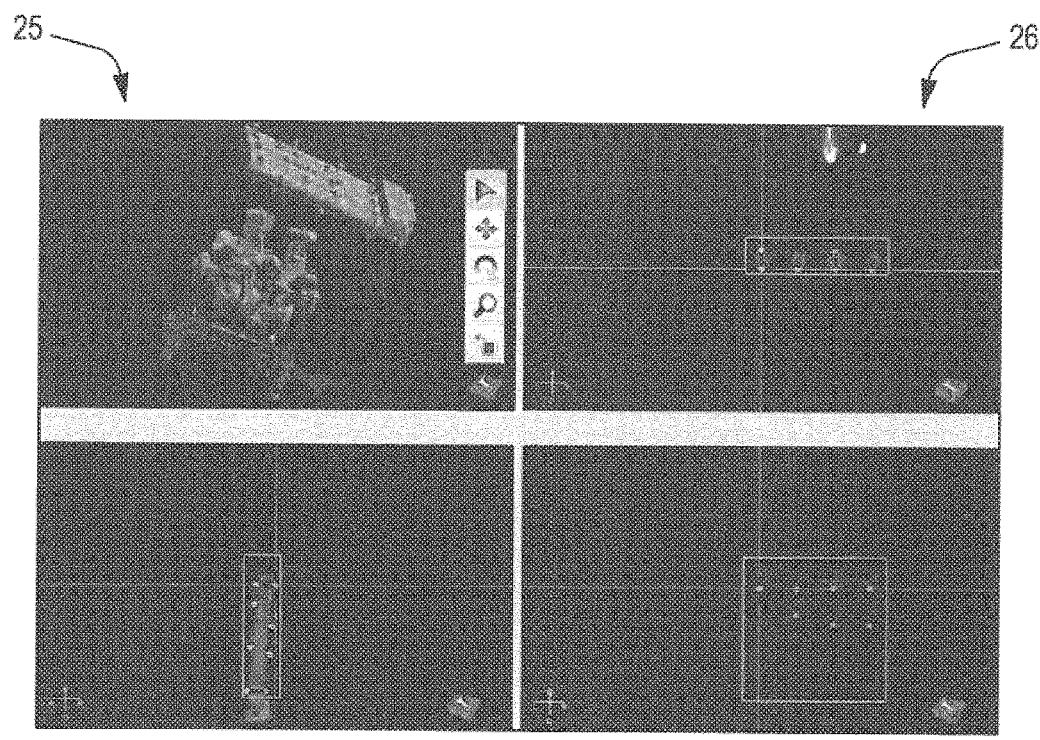
FIG. 13 is a representation of a technique for semi-automatically detecting the radiopaque fiducial markers of a recalibration device according to the invention.
Figure 14:
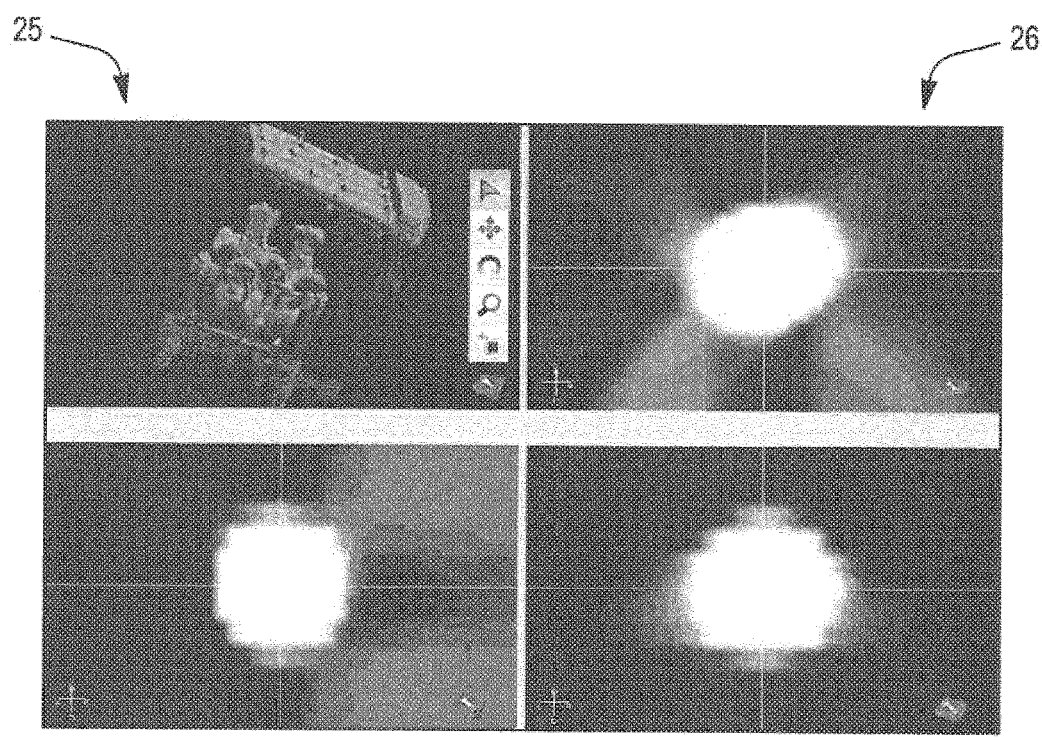
FIG. 14 is a representation of a technique for manually detecting the radiopaque fiducial markers of a recalibration device according to the invention.

For detecting each fiducial marker 9 in the three-dimensional digital model, there exist three methods, an automatic method, a semi-automatic method as illustrated in FIG. 13, and a manual method illustrated in FIG. 14.

In all three cases, a specific data processing software displays in a first window the three-dimensional digital model resulting from the acquisition of the anatomical area 2 of interest, in a second window 26 an image of an axial cross-section of the three-dimensional digital model, in a third window 27, an image of a sagittal cross-section of the three-dimensional digital model, and in a fourth window 28 an image of a coronal cross-section of said three-dimensional digital model. The user can thus "navigate" in the three-dimensional digital model while viewing the different cross-sections displayed by the software. He must then select the cross-sections in which are visible a maximum of fiducial markers 9, and preferably all the fiducial markers 9 of the recalibration device 1.

The manual identification technique illustrated in FIG. 14 consists in manually selecting with the aid of a cursor the center of each fiducial marker 9. The fiducial markers 9 can be identified in the three-dimensional digital model by means of their ghost image with a certain intensity. Once a fiducial marker 9 is identified in an image of the three-dimensional model, the operator selects it with the aid of the cursor, which generates a zoom on the desired portion of the image. The operator can then point with the cursor to the center of said fiducial marker 9. The software then records the coordinates of the positions of the centers of each fiducial marker 9 selected by the user in the reference system of the three-dimensional numerical model.

In order to assist the operator in selecting as well as possible the center of each fiducial marker 9, the selection of the center being made in a visual way, a software option permits, through a specific algorithm, once the fiducial marker 9 is manually selected by the operator, to identify the center of each fiducial marker 9 by calculating the weighted barycenter of each ghost image of the fiducial markers 9.

In the case of the semiautomatic identification technique illustrated in FIG. 13, the operator manually defines a box encompassing as many visible fiducial markers 9 as possible on each cross-section. This encompassing box permits to define a volume containing the fiducial markers 9 and to select all the fiducial markers 9 contained in the defined volume.

A specific algorithm then permits the automatic recognition in this defined volume, by using an intensity threshold effect, of the fiducial markers 9 in the three-dimensional digital model, by calculating the weighted barycenter of the apparent ghost images of the fiducial markers 9.

To this end, the luminous nature of each ghost image of fiducial markers 9 is used to distinguish the pixels corresponding to fiducial markers 9 from the pixels of the rest of each medical image. In practice, a luminance threshold is calculated, for each medical image, permitting to distinguish the pixels belonging to each fiducial marker 9, and then to calculate a weighted barycenter from these pixels. The luminance threshold corresponds to the value for which the number of pixels of the image corresponds to the number of pixels a disk with a 2 mm radius is comprised of. This disc corresponds to the intersection of a fiducial marker 9 of the recalibration device 1 with a plane passing through its center.

In the case of the automatic identification technique, a specific algorithm permits to automatically identify the fiducial, markers 9 present in the three-dimensional digital model by browsing the entire volume of the three-dimensional digital model, each ghost image of fiducial marker being identified by means of a luminance threshold representing the intensity of a fiducial marker 9 in medical pictures.

In order to ensure a certain detection of the recalibration device 1, a minimum of fiducial markers 9 must be detected. An insufficient number of fiducial markers 9, for example less than eight, would imply several solutions for detecting its orientation and would generate a lack of accuracy of the recalibration.

This extreme case can occur within the framework of each identification technique described above. The software then informs the user about the fact that there are not enough identified fiducial markers 9 to locate the recalibration device 1 in a certain way, which can generate detection errors, which, in turn, generate an inaccurate recalibration, which unavoidably leads to an inaccurate follow-up and operative guidance.

When a sufficient number of fiducial markers 9 are identified within the three-dimensional digital model, the software, knowing the geometric relationship between the navigation markers 10 of the recalibration device 1 and the fiducial markers 9, is capable of accurately locating the anatomical area 2 of interest in the reference system of the navigation system 23, of the robotic arm 22 and the patient.

Thus, the surgeon is able to plan the surgical operation during the step of planning the operation. The latter uses the recalibrated three-dimensional digital model. The surgeon can choose the type of tool or implant (e.g. pedicle screws the diameter and length of which can be parameterized by the surgeon), and then parameterize the most appropriate path for positioning the tools or implants. To this end, the surgeon can select a target point and an entrance point in the recalibrated three-dimensional model. The images of the tools and/or the implants can then be visualized, by superposition, on the images of the recalibrated three-dimensional model in order to simulate the operation in real time.

Figure 15:
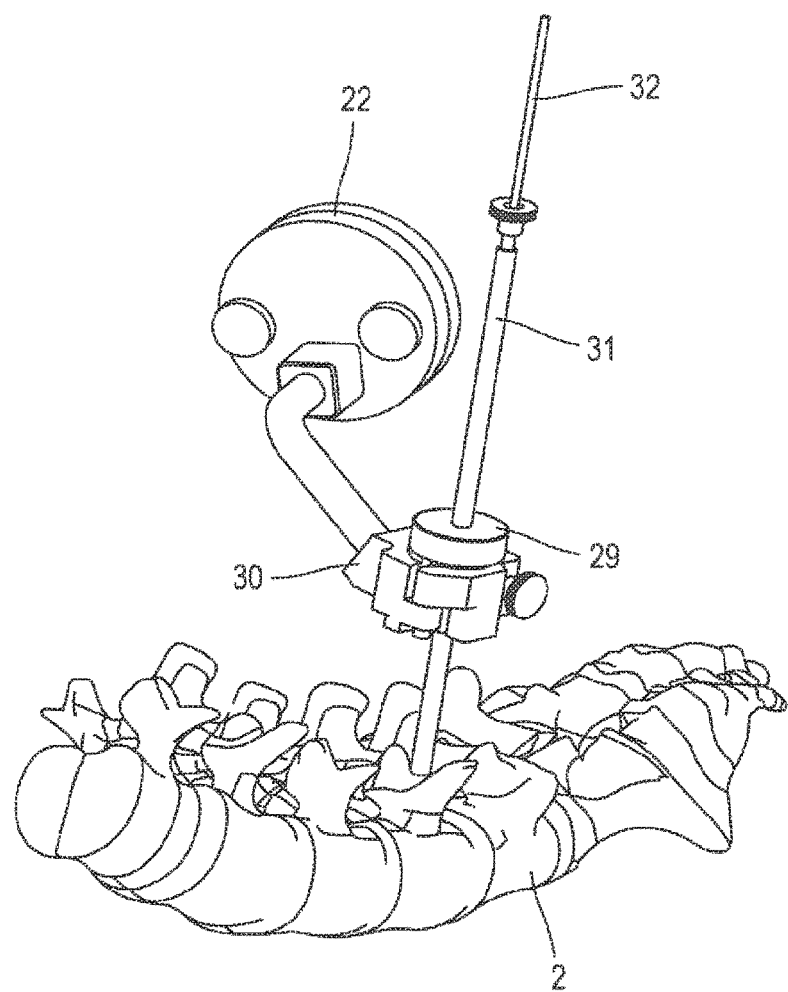
FIG. 15 is a perspective representation of a type of surgical operation that can be carried out after implementing a recalibration method using a recalibration device according to the invention.

As illustrated in FIG. 15, the operating protocol then comprises a step of preparing the robotic arm 22 for the surgical operation. In this step, the surgeon places an instrument holder 29 at a free end 30 of the robotic arm 22. The robotic arm 22 provided with the instrument holder is then guided on the trajectory previously defined in the planning step.

The surgical protocol then includes a piercing step in which the surgeon inserts a rigid cannula 31 into the instrument holder 29 until the bones of the vertebra to be pierced are reached. A drill 32 is inserted into the cannula 31 and brought into contact with the area to be drilled so as to form a hole in a pedicle. The drill 32 is removed and replaced by a second cannula finer than the rigid cannula 31, which permits to guide the insertion of a guiding pin into the body of the vertebra.

It should be noted that throughout this operation, the movements of the patient, namely related to his breathing, are monitored in real time by the navigation system 23. These movements of the patient can be taken into consideration so as to constrain the efforts exercised by the surgeon depending on the movements of the patient.

The invention claimed is:

1. A method of detecting a position and orientation of an anatomical area using a recalibration device as part of an image-guided surgical system, the method comprising:

accessing medical images of the anatomical area and the recalibration device positioned on a surface of the anatomical area;

generating a three-dimensional digital model from the medical images;

identifying radiopaque fiducial markers integrated into the recalibration device within the medical images, the radiopaque fiducial markers distributed spatially throughout a volume across multiple parallel planes within the recalibration device;

calculating a position and orientation of the recalibration device within a reference coordinate system of the anatomical area; and adjusting the three-dimensional digital model to the reference coordinate system of the anatomical area based on the position and orientation of the recalibration device; and generating a display of navigated instrument positions within the medical images, wherein the navigated instrument positions are tracked within the reference coordinate system by the image-guided surgical system.

2. The method of claim 1, wherein identifying the radiopaque fiducial markers includes identifying a specific geometrical pattern of at least a portion of the radiopaque fiducial markers.

3. The method of claim 2, wherein identifying the specific geometrical pattern includes identifying the specific geometrical pattern from a plurality of geometrical patterns formed by the radiopaque fiducial markers.

4. The method of claim 1, further comprising planning an operation using the three-dimensional digital model adjusted into the reference coordinate system.

5. The method of claim 1, further comprising tracking the anatomical area within the reference coordinate system based on navigation markers affixed to the recalibration device.

6. The method of claim 5, further comprising shifting the three-dimensional model within the reference coordinate system in accordance with tracking the anatomical area.

7. The method of claim 1, further comprising displaying a real-time image of the three-dimensional model in reference to the medical images of the anatomical area.

8. The method of claim 7, wherein displaying the real-time image includes displaying the three-dimensional model in reference to cross-sections of the anatomical area.

9. The method of claim 7, wherein displaying the real-time image includes displaying virtual representations of navigated instruments in reference the three-dimensional model.

10. An image-guided robot-assisted surgery system, the system comprising an optical navigation system and robotic arm, the system configured to perform operations comprising:

accessing medical images of the anatomical area and the recalibration device positioned on a surface of the anatomical area;

generating a three-dimensional digital model from the medical images;

identifying radiopaque fiducial markers integrated into the recalibration device within the medical images, the radiopaque fiducial markers distributed spatially throughout a volume across multiple parallel planes within the recalibration device;

calculating a position and orientation of the recalibration device within a reference coordinate system of the anatomical area;

adjusting the three-dimensional digital model to the reference coordinate system of the anatomical area based on the position and orientation of the recalibration device; and generating a display of an instrument positioned by the robotic arm overlaid on the medical images, wherein the instrument is tracked within the reference coordinate system by the optical navigation system.

11. The system of claim 10, wherein identifying the radiopaque fiducial markers includes identifying a specific geometrical pattern of at least a portion of the radiopaque fiducial markers.

12. The system of claim 11, wherein identifying the specific geometrical pattern includes identifying the specific geometrical pattern from a plurality of geometrical patterns formed by the radiopaque fiducial markers.

13. The system of claim 10, wherein the operations further include planning a procedure using the three-dimensional digital model adjusted into the reference coordinate system.

14. The system of claim 10, wherein the operations further include tracking the anatomical area within the reference coordinate system based on navigation markers affixed to the recalibration device.

15. The system of claim 14, wherein the operations further include shifting the three-dimensional model within the reference coordinate system in accordance with tracking the anatomical area.

16. The system of claim 10, wherein the operations further include displaying a real-time image of the three-dimensional digital model in reference to medical images of the anatomical area.

17. The system of claim 16, wherein displaying the real-time image includes displaying the three-dimensional digital model in reference to cross-sections of the anatomical area.

18. The system of claim 16, wherein displaying the real-time image includes displaying virtual representations of navigated instruments in reference the three-dimensional digital model.

19. A method of operating an image-guided surgical system to track a position and orientation of an anatomical area using a recalibration device during a surgical procedure, the method comprising:

acquiring medical images of the anatomical area including the recalibration device positioned on a surface of the anatomical area;

identifying radiopaque fiducial markers integrated into the recalibration device within the medical images, the radiopaque fiducial markers distributed spatially throughout a volume across multiple parallel planes within the recalibration device;

calculating a position and orientation of the recalibration device within a reference coordinate system of the anatomical area;

adjusting the medical images of the anatomical area to the reference coordinate system of the anatomical area based on the position and orientation of the recalibration device; and generating a display of navigated instrument positions within the medical images, wherein the navigated instrument positions are tracked within the reference coordinate system by an optical tracking system.

20. The method of claim 19, further comprising generating a three-dimensional model from the medical images, and wherein adjusting the medical images to the reference coordinate system includes adjusting the position and orientation of the three-dimensional model within the reference coordinate system based the position and orientation of the recalibration device.

* * * * *